United States Patent [19]

Cameron et al.

[11] Patent Number: 5,225,472
[45] Date of Patent: Jul. 6, 1993

[54] LOW VISCOSITY POLYTHIOL AND METHOD THEREFOR

[75] Inventors: Randy Cameron, Calabasas; Jonathan Zook, Santa Clarita, both of Calif.

[73] Assignee: Courtaulds Aerospace, Inc., Burbank, Calif.

[21] Appl. No.: 885,183

[22] Filed: May 19, 1992

[51] Int. Cl.$^5$ .............. C07C 323/18; C07C 323/19; C07C 323/12; C07C 323/09; C07C 323/03; C08K 5/37

[52] U.S. Cl. .................... 524/368; 524/392; 568/39; 568/49; 568/50; 568/51; 568/57

[58] Field of Search .............. 568/39, 50, 57; 525/535, 453, 440; 524/368, 392

[56] References Cited

U.S. PATENT DOCUMENTS

| | | | |
|---|---|---|---|
| 3,303,166 | 2/1967 | Bapseres et al. | 260/67 |
| 3,640,965 | 2/1972 | Brode et al. | 260/77.5 |
| 3,923,748 | 12/1975 | Hutt et al. | 260/77.5 |
| 4,366,307 | 12/1982 | Singh et al. | 528/373 |
| 4,425,389 | 1/1984 | Schollhorn et al. | 428/34 |
| 4,429,099 | 1/1984 | Kennedy et al. | 528/98 |
| 4,490,558 | 12/1984 | Bott | 568/58 |
| 4,609,762 | 9/1986 | Morris et al. | 568/38 |
| 4,623,711 | 11/1986 | Morris et al. | 528/375 |
| 4,689,395 | 8/1987 | Bergmann et al. | 528/374 |
| 5,087,758 | 2/1992 | Kanemura et al. | 568/57 |

FOREIGN PATENT DOCUMENTS

448224A1 9/1991 European Pat. Off. .

*Primary Examiner*—Veronica P. Hoke
*Attorney, Agent, or Firm*—Poms, Smith, Lande & Rose

[57] ABSTRACT

A method and composition for decreasing the viscosity of mercaptan terminated polymers. The method involves adding thiol terminated trithio-orthoformate polycondensates to the mercaptan terminated polymer to achieve desired decreases in viscosities without adversely affecting other physical properties. The polycondensates have the formula $$(HS-R-S-)_2CH-S-R'-S[-CH(-S-R'-S)_2-]_n(H)_x$$

wherein R, R', and R" are alkylene, arylene, alkylene thioether, or alkylene ether, either the same or different; n is 0-10; and x is n+1.

28 Claims, No Drawings

LOW VISCOSITY POLYTHIOL AND METHOD THEREFOR

BACKGROUND OF THE INVENTION

1. Field of the Invention

The present invention relates generally to mercaptan terminated polymers. More particularly, the present invention relates to synthesis of low viscosity polymeric polythiols and their use in compositions (and methods) for decreasing the viscosity of polymer formulations without the use of plasticizers or volatile organic components which decrease the viscosity at a cost to the final properties and are environmentally unacceptable.

2. Description of Related Art

Mercaptan terminated polymers are widely used in sealant, adhesive and coating compositions where quick or low temperature cures are needed. The polythioethers and polysulfides among this group also have good fuel, solvent, water and temperature resistance. Exemplary polymers within this group are described in U.S. Pat. Nos. 3,923,748; 4,355,307; 3,640,965; 4,425,389; 4,689,395 and 4,609,762.

The sealants, adhesives and coatings which contain these mercaptan terminated polymers are applied to surfaces as flowable liquids. In general, mercaptan terminated polymers have relatively high viscosities which make them difficult to formulate into viable finished products. One method for reducing the viscosity of the polymer compositions involves adding various volatile organic solvents to these compositions. Although the use of volatile diluents provides sufficient reduction in polymer viscosity, which results in easy to apply compositions, there are a number of drawbacks associated with the use of such volatile components. For example, the volatile diluents evaporate during the curing process and cause shrinking of sealant, adhesive or coating. In addition, the evaporating volatile components must be contained and dealt with in accordance with increasingly strict environmental regulations.

Another approach for providing flowable mercaptan terminated polymer sealants involves the use of plasticizers. Plasticizers eliminate shrinking problems because they do not evaporate from the polymer during the curing process. However, the plasticizer which remains in the cured sealant causes the sealant to have lower hardness and lower modulus. In many cases limited compatability of plasticizer and polymer results in slow phase separation leading to cracks in the applied materials. Blending of plasticizers also results in dirt collection at the surface of the applied compositions.

The problems associated with the use of volatile diluents and plasticizers become even more evident when compositions having increased hardness are desired. Increased hardnesses are typically achieved by adding extra filler to the formulation or adding hard aromatic segments to the polymer backbone. The use of extra filler or hard aromatic segments increases the viscosity resulting in decreased workability. To offset the increase in viscosity, extra organic diluent or plasticizers must be added. Additional filler may then have to be added to account for the extra diluent or plasticizers. This creates problems because excessive use of fillers decreases the elastomeric character of the final product.

It would be desirable to provide compositions and methods which do not rely on volatile organic diluents or plasticizers to lower viscosities. Such compositions and methods must be able to reduce the viscosity to a level which allows good workability without adversely affecting other desirable characteristics. For example, characteristics such as working time, curing time and long term stability should not be adversely affected by the compositions and methods used to reduce viscosity.

SUMMARY OF THE INVENTION

In accordance with the present invention, it was discovered that certain thiol terminated trithio-orthoformate containing polycondensates have very low viscosities in comparison to other mercaptan terminated polymers of similar molecular weight and mercaptan equivalence. The polycondensates which are useful in accordance with the present invention have the formula

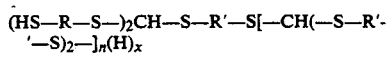

$$(HS-R-S-)_2CH-S-R'-S[-CH(-S-R'-S)_2-]_n(H)_x$$

wherein R, R', and R'' are alkylene, arylene, alkylene thioether, or alkylene ether, either the same or different; n is 0–10; and x is n+1.

As a feature of the present invention, the above-identified polycondensates may be used alone or in combination with a wide variety of other mercaptan terminated polymers to provide sealants, adhesives and coatings with viscosities that are low enough to minimize or eliminate the need for solvents and/or plasticizers. When used as an additive, the amount of polycondensate added to the mercaptan terminated polymer may be varied from about 1 to 99 weight percent depending upon the particular viscosity desired. The amount of polycondensate added to the mercaptan terminated polymer is directly related to the drop in viscosity of the resulting polymer blend. Accordingly, the polycondensates of the present invention may be used to provide compositions having a wide range of accurately controlled and selected viscosities.

As another feature of the present invention, the polycondensates may be added to a wide variety of mercaptan terminated polymers, including polysulfides, polyether urethanes, polyethers, and polythioethers, without adversely affecting desirable characteristics of the products. For example, when added in appropriate amounts, the polycondensates in accordance with the present invention do not affect the resistance of the resultant compositions to solvents and fuels or high temperatures. Further, it was discovered that the polycondensates actually improve a number of desirable characteristics of the cured compositions. Due to the high functionality of the polycondensates, the final cured materials have high hardness and tensile strength because of higher crosslink density. In addition, it was discovered that addition of the polycondensates increases the period during which the composition is workable. This increase in working period is achieved without also extending the overall curing time.

As an additional feature of the present invention, the polycondensates may be used alone or in combination with suitable polymers to provide adhesives, sealants and coatings having a low initial viscosity. The polycondensates may be added to not only control the viscosity, but also to control the working time and overall curing time of the adhesive, sealant or coating. The final cured coating or adhesive will be a strong elastic material due to the previously mentioned high functionality of the polycondensates of the present invention.

The above-discussed and many other features and attendant advantages of the present invention will become better understood by reference to the following detailed description of the invention.

DETAILED DESCRIPTION OF THE INVENTION

The present invention involves the synthesis of low viscosity polycondensate polythiols and their use in (and methods) for decreasing the viscosity of mercaptan terminated polymers without the use of volatile organic solvents or plasticizers. The polycondensates of the present invention may be added to a wide variety of mercaptan terminated polymers to achieve varying degrees of viscosity reduction. Suitable mercaptan terminated polymers include polythioethers, polysulfides, polythioether/polysulfide copolymers, polythioether polyurethanes, polyethers and other mercaptan terminated polymers which are used in sealants, adhesives or coatings. Exemplary mercaptan terminated polymers include those disclosed in U.S. Pat. Nos. 3,923,748; 4,609,762; and 4,366,307. The contents of these patent applications are hereby incorporated by reference. Specific preferred exemplary polymers include mercaptan terminated polymers available from Courtaulds Aerospace, Inc. (Woodland Hills, Calif.) under the tradenames PERMAPOL P3, PERMAPOL P5 and PERMAPOL P2. Preferred mercaptan terminated polymers are also available from Morton-Thiokol (Chicago, Ill.) under the tradename THIOKOL LP, Henkel Corp. (Morristown, N.J.) under the trademark CAPCURE and Baeyer A. G. (Leverkusen, Germany) under the tradename BAYTHIOL.

The polycondensates of the present invention may be used alone or in combination with other materials for a variety of purposes including formulation of sealants, adhesives and coatings. The following description will be limited to describing how to make exemplary polycondensates and how to use them as additives for decreasing the viscosity of mercaptan terminated polymers. It will be understood by those skilled in the art that the uses for the polycondensates in accordance with the present invention are not limited to the following described use as a viscosity decreaser for mercaptan terminated polymers, but that numerous other uses are possible.

The polycondensates in accordance with the present invention can be used alone or added to other mercaptan terminated polymers in amounts ranging from about 99 percent down to about 1 percent by weight of the overall polymer composition. The amount of polycondensate added to the mercaptan terminated base polymer depends upon the particular polymer and the desired viscosity of the uncured system and ultimate hardness of the cured system. The viscosities of the polycondensates in accordance with the present invention will typically range from between about 50 to 2000 centipoise. Mercaptan terminated polymers of the types disclosed in the above-identified patents have viscosities which range from between about 5000 to 500,000 cps.

The polycondensates in accordance with the present invention may be used to achieve decreases in the viscosities of the mercaptan terminated polymers on the order of 100 centipoise to 500,000 centipoise. Hardness of the cured mercaptan terminated polymers will increase on the order of 1 to 50 shore A. The amount of polycondensate added to the base polymer is directly related to the decrease in viscosity and increase in hardness. Accordingly, it is possible to control decreases in viscosity and increases in hardness by varying the amount of polycondensate which is added. The amount of polycondensate which is needed to achieve a desired reduction in viscosity or increase in hardness can be determined for a particular polymer by experimentation.

The thiol terminated trithio-orthoformate containing polycondensates in accordance with the present invention have the general formula

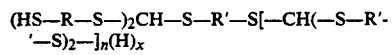

wherein R, R', and R" are alkylene, arylene, alkylene thioether, or alkylene ether, either the same or different; n is 0–10; and x is n+1.

R, R' and R" in the above formula are preferably an alkylene thioether or alkylene ether. A particularly preferred alkylene thioether is

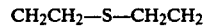

A particularly preferred alkylene ether is

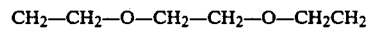

Although n in the above formula may range from 0 to 10, it is preferred that n be in the range of from 0 to 3. Polycondensates where R, R' and R" are the preferred alkylene thioether or alkylene ether set forth above and n is 0 are particularly preferred.

The polycondensates in accordance with the present invention may be made by condensing a dithiol with formic acid, a formate ester or a trialkylorthoformate in the presence of an acid catalyst. The condensation of dithiol with formic acid or ethyl formate occurs readily above 60° C. in the presence of catalytic amounts of an acid such as zinc chloride, toxic acid or boron trifluoride etherate. No reaction occurs without the catalyst being present. Reactions can occur at temperatures as low as 25° C., however, this requires larger amounts of catalyst or excess formate. Ethyl formate is preferred since it reacts more quickly than formic acid.

Numerous different dithiols may be used to react with formic acid or ethylformate to produce a variety of polycondensates in accordance with the present invention. A preferred dithiol for use in the condensation reaction is 2,2'[1,2-ethanediyl bis(oxy)] bis (ethanethiol) which is commonly referred to as DMDO. When DMDO is used as the only dithiol, the resulting polycondensate has a formula where R, R' and R" are $CH_2—CH_2—O—CH_2—CH_2—O—CH_2CH_2$. An alternative preferred dithiol is 2,2'-thiobis(ethanethiol) which is commonly known as DMDS. When DMDS is used as the dithiol in the condensation reaction, the resulting polycondensate has a formula where R is $CH_2CH_2—S—CH_2CH_2$.

Although DMDO or DMDS may be used to form polycondensates in accordance with the present invention, DMDO is preferred when higher molecular weight material is desired. In addition, when DMDS is used, boron trifluoride etherate is preferably used as the catalyst and ethyl formate is used as the other reactant since both ethylformate and boron trifluoride are soluble in DMDS.

The average molecular weight and resulting thiol equivalent weight of the polycondensate may be controlled by varying the ratio of formate to dithiol. For example, if one mole of formic acid is condensed with three moles of DMDO, the resulting product is, by and large, a low viscosity liquid having a molecular weight of 560 gm/mole. Other minor components in the product mixture are higher molecular weight polycondensates such as the pentamer, septamer and nonamer as well as residual unreacted dithiol.

In addition to decreasing viscosity and increasing hardness, the polycondensates in accordance with the present invention also increase the working time of the formulated compound. Increases in working time are on the order of a few minutes to an hour or more depending upon the particular polymer and the amount of polycondensate added. Working time is the period which begins with the addition of the catalyst or curing agent and ends when the viscosity of the composition increases to a point where the material cannot be easily applied to the surface being sealed. The polycondensates of the present invention provide an increase in working time without also increasing the overall cure time for the sealant.

To more fully illustrate the present invention, the following examples are presented:

EXAMPLE 1

300 grams of DMDO (1.648 moles), 16.5 grams of formic acid (0.549 moles), and 8.3 grams of zinc chloride were added into a three neck flask fitted with a mechanical stirrer, thermometer, and reflux condenser. These amounts of reactants provide the stoichiometry necessary to make a trithiol polycondensate where R, R' and R'' are $CH_2-CH_2-O-CH_2-CH_2-O-CH_2-CH_2$ and n=0. The mixture was heated to 85° C. and agitated for 9 hours. The mixture was allowed to cool while vacuum distilling to remove any unreacted monomers. The resulting polycondensate was a clear, colorless liquid having a viscosity of 70 centipoise and a thiol equivalent weight of 160 grams/equivalent (theory 185.3 grams/equivalent). The Fourier Transform Infrared (FT-IR) spectrum showed a reduction in the amount of thiol and absence of any significant amount of both carbonyl and hydroxyl absorbances indicating near complete reaction.

EXAMPLE 2

500 grams of DMDO (2.747 moles), 60.2 grams of formic acid (2.007 moles), and 10.0 grams of zinc chloride were added into a three neck flask fitted with a mechanical stirrer, thermometer, and reflux condenser. These amounts of reactants provide the stoichiometry necessary to make a dodecathiol polycondensate where R, R' and R'' are the same as in Example 1. The mixture was heated to 85° C. and agitated for 20.5 hours. The mixture was allowed to cool while vacuum distilling to remove any unreacted monomers. The resulting polycondensate had a thiol equivalent weight of 319 grams/equivalent (theory 327.6 grams/equivalent) and was a white insoluble solid. The FT-IR spectrum showed complete reaction.

EXAMPLE 3

368.7 grams of DMDO (2.026 moles), 50.1 grams of ethyl formate (0.667 moles), and 6.1 grams of zinc chloride were added into a three neck flask fitted with a mechanical stirrer, thermometer, and reflux condenser. These amounts of reactants provide the stoichiometry necessary to make a trithiol polycondensate where R, R' and R'' and n are the same as in Example 1. The mixture was heated to 85° C. and agitated for 6 hours. The mixture was allowed to cool while vacuum distilling to remove any unreacted monomers. The resulting polycondensate was a clear, colorless liquid having a viscosity of 60 centipoise and a thiol equivalent weight of 188 grams/equivalent (theory 185.3 grams/equivalent). The FT-IR spectrum showed complete reaction.

EXAMPLE 4

100 grams of DMDO (0.549 moles), 5.15 grams of formic acid (0.183 moles), and 2.0 grams of toxic acid were added into a three neck flask fitted with a mechanical stirrer, thermometer, and reflux condenser. These amounts of reactants provide the stoichiometry necessary to make a trithiol polycondensate where R, R' and R'' and n are the same as Example 1. The mixture was heated to 85° C. and agitated for 6.5 hours. The mixture was allowed to cool while vacuum distilling to remove any unreacted monomers. The resulting polycondensate was a clear, colorless liquid having a thiol equivalent weight of 196 grams/equivalent (theory 185.3 grams/equivalent). The FT-IR spectrum showed complete reaction.

EXAMPLE 5

In order to prepare a higher molecular weight dithiol, DMDO was extended via formation of a thioacetal linkage as follows: 300 grams of DMDO (1.648 moles), 59.5 grams of 2-butanone (0.826 moles), and 5.25 grams of zinc chloride were added to a three neck flask fitted with a mechanical stirrer, thermometer, and reflux condenser. The mixture was stirred at 25° C. for three hours. The resulting extended dithiol had a thiol equivalent weight of 165.4 grams/equivalent (theory 209 grams/equivalent).

The trithio-orthoformate containing polycondensate was then formed as follows: To 361 grams of the extended dithiol produced using the above procedure was added 13.8 grams of formic acid (0.460 moles). The mixture was heated to 85° C. in a three neck flask fitted as described above and agitated under reflux conditions for 8 hours. The mixture was allowed to cool while vacuum distilling to remove any unreacted monomers. The resulting polycondensate, unlike the material produced in Example 2, was a clear, colorless liquid. For this Polycondensate, R is an alkyl substituted thioether/thioacetal and n is 0. The thiol equivalent weight of this material was 308 grams/equivalent (theory 334 grams/equivalent) and the viscosity was 115 centipoise. The FT-IR spectrum indicated near complete reaction.

EXAMPLE 6

600 grams of DMDS (3.896 moles), 250 grams of 2-butanone (3.472 moles), 96 grams of ethyl formate (1.297 moles), and 8.6 grams of boron trifluoride etherate were added into a three neck flask fitted with a mechanical stirrer, thermometer, and reflux condenser. These amounts of reactants provide the stoichiometry necessary to dimerize the DMDS and form the trithiol polycondensate directly. The mixture was heated to 85° C. and agitated for 6 hours. The mixture was allowed to cool while vacuum distilling to remove any unreacted monomers. The resulting polycondensate was a clear, colorless liquid having a thiol equivalent weight of 259 grams/equivalent. R, R', R'' and n for this polycondensate are the same as in Example 5. The FT-IR spectrum showed complete reaction.

EXAMPLE 7

206.4 grams of DMDO (1.134 moles), 40 grams of formic acid (0.870 moles) and 2.0 grams of a 50% by weight toxic acid in methanol solution were added into a three neck flask fitted with a mechanical stirrer, thermometer, and reflux condenser. The mixture was agitated for 24 hours at room temperature (25° C.) and vacuum distilled to remove any unreacted monomers. The resulting polycondensate was a clear, colorless liquid having a viscosity of 78 centipoise and a thiol equivalent weight of 150 grams/equivalent. The FT-IR spectrum showed complete reaction.

EXAMPLE 8

149.0 grams DMDS were added to 31.0 grams ethyl formate and 3.0 grams boron trifluoride etherate. This mixture was heated at 100° C. for 8 hours. The mixture was then vacuumed to remove ethanol, water or unreacted ethyl formate. The resulting clear liquid had a mercaptan equivalence of 120 grams/equivalent. The viscosity of the material was 67 centipoise. The FT-IR spectrum showed complete reaction.

EXAMPLE 9

Blends containing varying amounts of the polycondensate of Example 8 in Thiokol LP-31 were prepared and formulated by mixing 43 grams of calcium carbonate per 100 grams of polymer mixture. The viscosities, in centipoise, were determined at 25° C. using a Brookfield model RTVD viscometer. The cure hardness, measured in Shore A hardness units, was determined by admixing the formulated polymer-polycondensate blend with a manganese dioxide paste consisting of a 50:50 mixture of manganese dioxide and hydrogenated terphenyl plasticizer. The manganese dioxide paste to formulate polymer-polycondensate blend ratio was 10:100 and the cure hardness was measured after 24 hours at 25° C. and 50% relative humidity. The results are compared in the table below:

| Percent of Polycondensate of Example 8 in the Thiokol LP-31 Blend | | | | | | | |
|---|---|---|---|---|---|---|---|
| 0 | | 10 | | 20 | | 40 | |
| Viscosity | Hardness | Viscosity | Hardness | Viscosity | Hardness | Viscosity | Hardness |
| 280,000 | 45 | 220,800 | 50 | 176,000 | 57 | 71,200 | 60 |

EXAMPLE 10

74.5 grams of DMDS (0.484 moles), 88.0 grams of DMDO (0.484 moles), 31.0 grams of ethyl formate (0.484 moles), and 3.0 grams of boron trifluoride etherate were added to a three neck flask fitted with a mechanical stirrer, thermometer, and reflux condenser. The mixture was stirred at 100° C. for eight hours. The mixture was allowed to cool while vacuum distilling to remove any unreacted monomers. The resulting polycondensate was a clear, colorless liquid. The thiol equivalent weight of this material was 174 grams/equivalent and the viscosity was 73 centipoise. The FT-IR spectrum indicated near complete reaction.

EXAMPLE 11

Polymer blends containing varying amounts of the polycondensate of Example 2 were prepared and the viscosity and cure hardness determined. The viscosities were determined at 25° C. using a Brookfield model RTVD viscometer. The cure hardness was determined by admixing the polymer-polycondensate with the commercially available diglycidyl ether bisphenol A resin, Epon 828. The epoxide to thiol ratio was 1.0, a small amount (0.1% by weight) of diazabicyclooctane (DABCO) was added as a catalyst, and the cure hardness was measured after 24 hours at 25° C. and 50% relative humidity. The results are compared in the table below:

| Thiol Terminated Polymer | Weight Percent of Polycondensate of Example 2 Added to Polymer | | | |
|---|---|---|---|---|
| | 0 | | 15 | |
| | Viscosity | Hardness | Viscosity | Hardness |
| Permapol P2-805, U.S. Pat. No. 3,923,748 | 2,864 poise | 28 Shore A | 976 poise | 38 Shore A |
| Permapol P5-960, U.S. Pat. No. 4,623,711 | 148 poise | 28 Shore A | 44 poise | 35 Shore A |
| Capcure 3-800, Thiol Functional Oligomer Marketed by Henkel Corp. | 160 poise | 65 Shore A | 44 poise | 67 Shore A |
| Thiol Terminated Polymer Prepared According to U.S. Pat. No. 3,446,780 | 1,080 poise | 8 Shore | 218 poise | 20 Shore A |

Having thus described exemplary embodiments of the present invention, it should be noted by those skilled in the art that the within disclosures are exemplary only and that various other alternatives adaptations and modifications may be made within the scope of the present invention. Accordingly, the present invention is not limited to the specific embodiments as illustrated herein but is only limited by the following claims.

What is claimed is:

1. A composition of matter comprising a thiol terminated trithio-orthoformate containing polycondensate having the formula

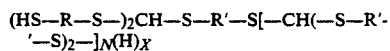

$$(HS-R-S-)_2CH-S-R'-S[-CH(-S-R'-S)_2-]_N(H)_X$$

wherein R, R', and R" are alkylene, arylene, alkylene thioether or alkylene ether, either the same or different; N is 0–10; and X is N+1.

2. A composition of matter according to claim 1 wherein R and R' are the same.

3. A composition of matter according to claim 1 wherein R and R" are the same.

4. A composition of matter according to claim 1 wherein R' and R" are the same.

5. A composition of matter according to claim 2 wherein R" is the same as R and R'.

6. A composition of matter according to claim 1 wherein R, R' or R" are $CH_2CH_2-S-CH_2CH_2$.

7. A composition of matter according to claim 1 wherein R, R' or R" are $CH_2-CH_2-O-CH_2-CH_2-O-CH_2CH_2$.

8. A composition of matter according to claim 6 wherein n is from 0 to 3.

9. A composition of matter according to claim 7 wherein n is from 0 to 3.

10. A composition of matter according to claim 5 wherein R, R' or R" are CH$_2$CH$_2$—S—CH$_2$CH$_2$ and n is 0.

11. A composition of matter according to claim 5 wherein R, R' or R" are CH$_2$—CH$_2$—O—CH$_2$—CH$_2$—O—CH$_2$CH$_2$ and n is 0.

12. A composition of matter according to claim 1 which further includes from about 1 to 99 weight percent of a mercaptan terminated polymer.

13. A composition of matter according to claim 12 wherein R and R' are the same.

14. A composition of matter according to claim 12 wherein R and R" are the same.

15. A composition of matter according to claim 12 wherein R' and R" are the same.

16. A composition of matter according to claim 13 wherein R" is the same as R and R'.

17. A composition of matter according to claim 12 wherein R, R' and R" are CH$_2$CH$_2$—S—CH$_2$CH$_2$ and n is from 0 to 3.

18. A composition of matter according to claim 12 wherein R, R' and R" are CH$_2$—CH$_2$—O—CH$_2$—CH$_2$—O—CH$_2$CH$_2$ and n is from 0 to 3.

19. A composition of matter according to claim 16 wherein R, R' and R" are CH$_2$CH$_2$—S—CH$_2$CH$_2$ and n is 0.

20. A composition of matter according to claim 16 wherein R, R' and R" are CH$_2$—CH$_2$—O—CH$_2$—CH$_2$—O—CH$_2$CH$_2$ and n is 0.

21. In a mercaptan terminated polymer wherein said mercaptan terminated polymer is applied as a flowable material having a viscosity, the improvement comprising adding a sufficient amount of thiol terminated trithio-orthoformate containing polycondensate to said thiol terminated polymer to decrease the viscosity of said polymer, said polycondensate having the formula

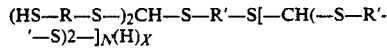

wherein R, R', and R" are alkylene, arylene, alkylene thioether or alkylene ether, either the same or different; N is 0–10; and X is N+1.

22. An improved mercaptan terminated polymer according to claim 21 wherein said polymer is selected from the group consisting of mercaptan terminated polythioether, mercaptan terminated polysulfide, mercaptan terminated polythioether/polysulfide copolymer, mercaptan terminated polyether polyurethane and mercaptan terminated polyether.

23. An improved mercaptan terminated polymer according to claim 22 wherein R, R' and R" are CH$_2$CH$_2$—S—CH$_2$CH$_2$ and n=0.

24. An improved mercaptan terminated polymer according to claim 22 wherein R, R' and R" are CH$_2$—CH$_2$—O—CH$_2$—CH$_2$—O—CH$_2$CH$_2$ and n=0.

25. A method for decreasing the viscosity of a mercaptan terminated polymer, said method comprising the steps of adding to said polymer a sufficient amount of thiol terminated trithio-orthoformate containing, said polycondensate to decrease the viscosity of said polymers, said polycondensate having the formula

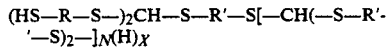

R, R', and R" and alkylene, arylene, alkylene thioether, or alkylene ether, either the same or different; N is 0–10; and X is N+1.

26. A method according to claim 25 wherein said polymer is selected from the group consisting of mercaptan terminated polythioether, mercaptan terminated polysulfide, mercaptan terminated polythioether/polysulfide copolymer, mercaptan terminated polyether polyurethane, and mercaptan terminated polyether.

27. A method according to claim 25 wherein R, R' and R" are CH$_2$CH$_2$—S—CH$_2$CH$_2$ and n=0.

28. A method according to claim 25 wherein R, R' and R" are CH$_2$—CH$_2$—O—CH$_2$—CH$_2$—O—CH$_2$CH$_2$ and n=0.

* * * * *